US007097617B1

(12) United States Patent
Smith

(10) Patent No.: US 7,097,617 B1
(45) Date of Patent: Aug. 29, 2006

(54) METHOD FOR DIAGNOSIS OF PAIN RELIEF PROBABILITY THROUGH MEDICAL TREATMENT

(76) Inventor: Wallace Lynn Smith, 2621 S. Wolff Way, Denver, CO (US) 80219

( * ) Notice: Subject to any disclaimer, the term of this patent is extended or adjusted under 35 U.S.C. 154(b) by 79 days.

(21) Appl. No.: 10/813,080

(22) Filed: Mar. 31, 2004

(51) Int. Cl.
*A61B 5/00* (2006.01)

(52) U.S. Cl. ........................ 600/300; 128/898
(58) Field of Classification Search ........ 600/300–301, 600/545, 599; 434/235–238; 128/897–898
See application file for complete search history.

(56) References Cited

U.S. PATENT DOCUMENTS

| | | | |
|---|---|---|---|
| 5,486,999 | A | 1/1996 | Mebane |
| 5,882,203 | A | 3/1999 | Correa et al. |
| 5,961,332 | A | 10/1999 | Joao |
| 6,053,739 | A | 4/2000 | Stewart et al. |
| 6,093,026 | A | 7/2000 | Walker et al. |
| 6,338,039 | B1 | 1/2002 | Lonski et al. |
| 6,425,764 | B1 | 7/2002 | Lamson |
| 2002/0128868 | A1 | 9/2002 | Lonski et al. |
| 2003/0055679 | A1 | 3/2003 | Soll et al. |
| 2003/0059750 | A1 | 3/2003 | Bindler et al. |
| 2003/0108849 | A1 | 6/2003 | Hodges |
| 2003/0162156 | A1 | 8/2003 | Poreh |
| 2003/0180698 | A1 | 9/2003 | Salerian |

OTHER PUBLICATIONS

Hamlin, Hitchcock, Hofmeister, and Owens, Predicting Surgical Outcome for Pain Relief and Return to Work, Best Practices and Benchmarking Healthcare, Sep./Oct. 1996, pp. 258-261, vol. 1, No. 5, Mosby-Year Book, Inc., St. Louis, U.S.A.

Smith, Paindex Test Booklet, 1997, pp. 1-9, Cortical Function Laboratory, Inc., Denver, U.S.A.

(Continued)

*Primary Examiner*—Max F. Hindenburg
*Assistant Examiner*—Michael C. Astorino
(74) *Attorney, Agent, or Firm*—William L. MacBride, Jr.; Gough, Shanahan, Johnson & Waterman

(57) ABSTRACT

The present invention pertains to a method of diagnosing patients having chronic pain as medically unexplained symptoms, or somatization, in order to assess a probability of relief of such pain through medical treatment. The present invention is a self-reporting diagnostic test that identifies and quantifies psychological and behavioral factors that can affect treatment outcome for a patient sensitive to somatization, that might have a bearing on a decision by a physician to operate or otherwise medically treat a patient, and the problems that could occur post-operatively or after treatment. The method of the present invention diagnoses a probability of pain relief through medical treatment in a patient by administration of a test comprised of declarative statements of validity factors comprising defensiveness, predictiveness and carelessness, and clinical factors comprising somatic concern, depressed mode, passive personality, compulsive/obsessive personality, hypomania, and ego integrative defect. From the raw scores for each of the six (6) clinical factors, a scoring value of standard deviations above the normative group mean is calculated, enabling the clinician to produce a single numerical index score indicating and measuring the effect of somatization on the patient.

2 Claims, 15 Drawing Sheets

OTHER PUBLICATIONS

Greene, The MMPI-2/MMPI: an Interpretive Manual, 1991, pp. 37-38, 65-68, 117-118, 136-138, 140-148, 164-167, 172-175 and 186-188, Allyn and Bacon, Boston, U.S.A.

Smith and Duerksen, Personality and the Relief of Chronic Pain: Predicting Surgical Outcome, clinical Neuropsychology, 3rd Qtr. 1979, pp. 35-38, U.S.A.

Dhanens and Jarrett, MMPI Pain Assessment Index: Concurrent and Predictions Validity, The Intl. J. of Clinical Neuropsychology, 1984, pp. 46-48, vol. VI, U.S.A.

Turner, Herron and Weiner, Utility of the MMPI Pain Assessment Index in Predicting Outcome After Lumbar Surgery, J. of Clinical Psychology, Sep. 1986, pp. 764-769, vol. 42, No. 5, Dept. of Psychiatry and Behavioral Sciences RP 10, U. of Washington, Seattle, U.S.A.

PAINDEX® Predictive Equation

501

Female Probabilities of Success

When the 8 item score is:   The predicted probability of success is:

| Score | Probability |
|---|---|
| 8 | 96.77% |
| 7 | 93.6% |
| 6 | 88.3% |
| 5 | 80.8% |
| 4 | 70.5% |
| 3 | 58.7% |
| 2 | 45.6% |
| 1 | 33.4% |
| 0 | 22.7% |

502

Male Probabilities of Success

When the 8 item score is:   The predicted probability of success is:

| Score | Probability |
|---|---|
| 1 | 15% |
| 2 | 35% |
| 3 | 48% |
| 4 | 61% |
| 5 | 75% |
| 6 | 85% |
| 7 | 93% |
| 8 | 97.8% |

Smoother Values for Men

Paindex®
SCORING VALUES

Code for subtests
D (defensiveness)
O (Owens Predictive Equation)
C (carelessness)

Summary of Values
1 = S (somatic)
2 = M (mood)
3 = Y (hysteria)
4 = T (OB comp)
5 = H (hypomania)
6 = E (ego integrative defect)

1 / 4 = S/T (fear)
1 / 3 = S/Y (anxiety)
1 / 5 = M/H (self esteem)

Total Value _____

R = Raw Score
A = Adjusted Score for D added to TSH raw score
F = Final Score
V = Value Score t = Standardized Score D Score Adjustments

| T | S | H |
|---|---|---|
| 30 | 15 | 6 |
| 29 | 15 | 6 |
| 28 | 14 | 6 |
| 27 | 14 | 5 |
| 26 | 13 | 5 |
| 25 | 13 | 5 |
| 24 | 12 | 5 |
| 23 | 12 | 5 |
| 22 | 11 | 4 |
| 21 | 11 | 4 |
| 20 | 10 | 4 |
| 19 | 10 | 4 |
| 18 | 9 | 4 |
| 17 | 9 | 3 |
| 16 | 8 | 3 |
| 15 | 8 | 3 |
| 14 | 7 | 3 |
| 13 | 7 | 3 |
| 12 | 6 | 2 |
| 11 | 6 | 2 |
| 10 | 5 | 2 |
| 9 | 5 | 2 |
| 8 | 4 | 2 |
| 7 | 4 | 1 |
| 6 | 3 | 1 |

*t* Scoring Rules

124 — *tS*: S score, convert raw score to *t* score. 55*t* is baseline (for both male and female). For each 5 points above 55*t* add 1 point, i.e., for *t* of 65 add 2 points, *t* of 70 add 3, etc. for S score final value

129 — *tS-tT*: S(*t*) Score higher than T(*t*) Score 11 or more points = Value Score of 2

128 — *tS-tY*: S Score (*t*) equal to or higher (*t*) than Y Score = Value Score of 2

125 — *tM*: M Scores (*t*)
Male 61 and up = Value of 3
Female 61 and up = Value of 3

130 — *tM-tH*: M / H (*t*)
Male / Female M 6 or more *t* scores above H = Value of 2

126 — *tY*: Y Scores (*t*)
Male 85 and up = Value of 7
 72 thru 84 = Value of 2
Female 86 and up = Value of 7
 79 thru 85 = Value of 2

127 — E Scores (R):
Male 57 to 47 = 1
 46 to 37 = 2
 36 to 26 = 3

Female 53 to 45 = 1
 44 to 32 = 2
 31 to 21 = 3

FIG. 14

METHOD FOR DIAGNOSIS OF PAIN RELIEF PROBABILITY THROUGH MEDICAL TREATMENT

BACKGROUND

The present invention pertains to a method of diagnosing patients having chronic pain as medically unexplained symptoms, or somatization as defined in *Taber's Cyclopedic Medical Dictionary*, F. A. Davis Co., Philadelphia, 1993, in order to assess a probability of relief of such pain through medical treatment. In particular, the present invention is a self-reporting diagnostic test that identifies and quantifies certain psychological and behavioral, or clinical factors. These clinical factors can affect medical treatment outcome for a patient sensitive to somatization. Any identified effect of such a condition on potential medical treatment outcome will have a critical bearing on a decision by a physician to operate or otherwise medically treat a patient, and on predicting problems that could occur post-operatively or after treatment.

Failure in predicting outcome for treatment aimed at pain relief has been one of the most costly problems facing healthcare delivery systems today. It is estimated that ten percent (10%) of medical services in the United States are delivered to patients with no evidence of organic disease, and the cost of this care is estimated to be twenty billion dollars ($20,000,000,000) annually. The cost of failing to detect such high-risk patients are staggering, as twenty percent (20%) of all patients account for eighty percent (80%) of the available dollars for treatment.

DESCRIPTION OF THE RELATED ART

Persons skilled in the art recognize that psychological problems are an important factor in assessing the success of surgeries on patients for obtaining pain relief. In increasing numbers, physicians and surgeons are seeking assistance with diagnoses of patients with chronic pain as medical symptoms without identified pathology. However, there is almost no support in medical literature for psychological/psychiatric assessment as a reliable predictor of surgical outcome or other medical treatment for the pain relief. Charles Hamlin, Michael Hitchcock, John Hofmeister, and Robert Owens, "Predicting Surgical Outcome for Pain Relief and Return to Work," Best Practices and Benchmarking Healthcare, Mosby-Year Book, Inc., Vol. 1, No. 5 (Sep./Oct. 1996), St. Louis, pp. 258–261. The present invention identifies and quantifies psychological problems and predicts, to a high statistical probability, the probability of patient pain relief, where symptoms do not correspond with diagnostic studies and/or physical symptoms. Hamlin, Hitchcock and Hofmeister, p. 258.

The related art provides methods and systems for health care data management and other industries and industrial plant facilities, for categorizing healthcare treatment, and for utilizing computer systems involving patient interaction with a testing or screening mechanism. The related art also provides for techniques for detecting and diagnosing the presence of depression and other psychological disorders. There clearly exists a need in the art, as demonstrated by the literature, for a method invention as a reliable predictor of somatization to assist physicians and their patients exhibiting symptoms of the somatization medical disorder, in deciding whether to go forward with a chosen form of medical treatment.

There is limited art related to methods for assessing mental or psychological disorders in patients, but no art for testing the probability of pain relief in the presence of somatization, as in the present invention. As a co-morbidity test in medical/surgical patients, the present invention is the only testing procedure known to be available that is a diagnostic assessment of the mind-body interface, thereby testing the perception to pain, and analyzing the impact of somatization.

Information relevant to this area of related art can be found in prior patents. Much of the related art discloses healthcare management systems or general treatment systems. U.S. Patent Number 2003/0180698 A1 to Salerian discloses a screening tool to rapidly (within one minute) determine the presence of a mental disorder in a patient. Patient evaluation is facilitated in Salerian by a visual assessment (color coded indicator) of an initial condition and a progressive response to treatment.

Other related art identifies mental or psychological disorders in patients. U.S. Pat. No. 5,882,203 to Correa et al. relates to a method of psychological testing to detect depression and its severity by means of color perception by a patient. U.S. Patent Number 2003/0055679 A1 to SOLL et al. relates to medical treatment system analyses input from patient and physician to diagnose a medical complaint. U.S. Pat. No. 6,425,764 B1 to Lamson relates to a computer-generated environment, or virtual reality, for assessment, prevention and treatment of psychiatric conditions; utilizing visual, auditory and tactile sensory stimulation and feedback, and U.S. Pat. No. 6,053,739 to Stewart et al. relates to diagnosing educational disabilities by use of a visual computer display and recording responses to predetermined visual test targets. U.S. Patent Number 2003/0108849 A1 to Hodges discloses a method for evaluating health or personality scores of children from Child and Adolescent Functional Assessment Scale tests.

Other related art discloses computer-based healthcare data management methods. U.S. Pat. No. 5,486,999 to Mebane relates to assessing and categorizing different forms of healthcare utilized by patients. U.S. Pat. No. 5,961,332 to Joao relates to a method for acquisition, accumulation, analysis and application of psychological and/or psychopathological data and other information. U.S. Patent Number 2003/0162156 A1 to Porch relates to methods of recording healthcare test data from a psychological test utilizing computer storage. U.S. Patent Number 2003/0059750 A1 to Bindler et al. relates to a patient interactive system for providing automated, online computer based psychological services of varying types. U.S. Patent Numbers 2003/0128868 A1 and 6,338,039 B1, to Lonski et al. relate to methods for automating the gathering of patient information. U.S. Pat. No. 6,093,026 to Walker et al. relates to a method for preparing and administering information surveys conducted in varying fields.

Medical journals have reported from clinical observations that certain psychological and behavioral factors are associated with poor surgical outcomes and delayed recoveries, and that these factors may represent complex and long-standing personality traits in patients. However, until the present invention, no effective diagnostic tool, or method, has been developed to accurately predict the probability of pain relief. Hamlin, Hitchcock and Hofmeister, p. 258.

The Minnesota Multiphasic Personality Inventory Test ("MMPI") is a widely used, standardized personality test for the diagnosis of psychopathology and personality attitudes and characteristics. Related art does use the self-reporting format for testing personality, such as the MMPI. However, there exists in the related art a need for a medical diagnostic test of somatization.

The present invention is not a personality test; an advantage of the present invention is that it is a medical diagnostic test through a combination of patient behavioral and perceptual configurations set forth in a method testing procedure. Earlier work in the area of diagnosing perception to pain for predicting treatment outcome was abandoned by other clinicians for lack of significant predictability. Initial work by the Inventor poorly predicted the probability of pain relief for patients, and only predicted the probability of pain relief for certain medical conditions (laminectomy patients and carpal tunnel patients). In those specific cases, sensitivity test scores (a percentage ability of the testing method to identify and predict somatizers) and specificity test scores (a percentage ability of the testing method to identify and predict non-somatizers) matched poorly and were not diagnostic of actual patient clinical outcomes. Prior pain perception testing methods developed by the Inventor demonstrated a difference between then-current, sensitivity scores and specificity scores. A gap in results between sensitivity and specificity percentages represented a predictive failure in prior testing methods to adequately diagnose somatization. The inability to close the gap in original testing methods affected the predictive accuracy of the earlier tests in any related art.

Broadly, it is the object of the present invention to provide a diagnostic tool assessing the effects of somatization in order to accurately predict the probability of pain relief after surgery. There is no existing method or combination of methods that perform the same function in a different way, or similar way, to the present invention.

SUMMARY

An object of the present invention is to be a method for analyzing a patient's perception of pain and thereby the probability of pain relief through medical treatment. Another object of the present invention is a patient self-reporting test method consisting of applied algorithm and assessment scores that identify and quantify certain clinical (psychological and behavioral) factors that may affect treatment outcome for a patient sensitive to somatization. The Inventor has marketed a number of analyses/tests for psychological/psychiatric assessment as predictors of surgical outcome for pain relief under the trademark Paindex®, with varying degrees of predictive success. The present invention enables the medical community, for the first time, using a diagnostic test, to assess somatization effects and reliably predict a probability for pain relief from the incorporation of all of the psychological and behavioral factors that might have a bearing on a decision to operate and the problems that may occur after surgery.

The present invention yields two independent predictive diagnostic values: a "Pain Index Score" and a "Probability Equation Score." The Probability Equation Score was developed by the Inventor, in part, by using logarithmic regression equations from the MMPI. The Probability Equation Score and the Pain Index Score are generated in the present invention by predictive algorithms derived from patient responses to declarative statements in a test given to the patient. Declarative statements are taken from the MMPI, and utilized for psychopathology and personality situations identified by the Inventor, to predict the impact of the clinical (psychological and behavioral) factors on surgical or treatment outcome for a patient.

The individual patient responses are categorized into three (3) test validity factor scales and six (6) clinical factor scales to yield a graphic profile of the clinical factors that can be evaluated statistically. The Pain Index Score is calculated from the six clinical factor templates developed by the Inventor. The Probability Equation Score is calculated utilizing predictive probability equations developed from clinical observations by the Inventor. These two independent predictive values, the Pain Index Score and the Probability Equation Score, are compared and reported to surgeons as the statistical probability of pain relief in the present invention.

The present invention overcomes the shortcomings of earlier related art and the Inventor's earlier failure to accurately predict the probability of pain relief by medical treatment, due to a lack of balance between the sensitivity scores and the specificity scores to achieve an acceptable predictability result. The Inventor has determined that chronic somatizers have a poor sense of self (i.e., a weak ego), a critical component missing in earlier clinical factors, which led to a use of an ego integrative defect scale (the "E" clinical factor) further described below. Another advantage of the present invention is the recognition and quantification of this additional E factor. This correction to the method resulted in an E scale being utilized in the invention, closing the gap between sensitivity and specificity scores, which balanced the testing method of the present invention and proved the predictive accuracy to an acceptable level, in the middle to high ninety percent (90%), as independently observed by medical physicians.

Underlying the present invention is the recognition that certain clinical factors (psychological and behavioral factors) determine a patient's perception of pain relief, which in turn will determine the success of medical treatment to relieve such pain, all as will be better understood as the description of the present invention proceeds. The description of the present invention, together with the accompanying drawings should not be construed as limiting the present invention to the example shown and described, because those skilled in the art to which this invention appertains will be able to devise other forms thereof within the ambit of the appended claims. The aforementioned features, aspects and advantages of the present invention, and further objectives and advantages of the present invention, will become apparent from a consideration of the drawings and ensuing description.

BRIEF DESCRIPTION OF THE DRAWINGS

The method of the present invention will be better understood by reference to the following description taken in connection with the accompanying drawings in which:

FIG. 2 Shows a response sheet, entitled Scores for Paindex®, to record patient responses to the declarative statements and subsequent scoring values.

FIG. 3 Shows a response template to score the patient's "D" (defensiveness) validity factor responses.

FIG. 4 Shows a response template to score the patient's "O" (predictiveness) validity factor responses.

FIG. 5 Shows a Paindex® Predictive Equation model for determining probability equation score percentages.

FIG. 6 Shows a response template to score the patient's "C" (carelessness) validity factor responses.

FIG. 10 Shows a response template to score the patient's "T" (compulsive/obsessive) clinical factor responses.

FIG. 11 Shows a response template to score the patient's "H" (hypomania) clinical factor responses.

FIG. 12 Shows a response template to score the patient's "E" (ego integrative defect) scale clinical factor responses.

FIG. 14 Shows a Paindex® Scoring Value set of scoring rules or group of equations to be applied to the t scores for the clinical factors.

DETAILS OF THE INVENTION

Figure 1:
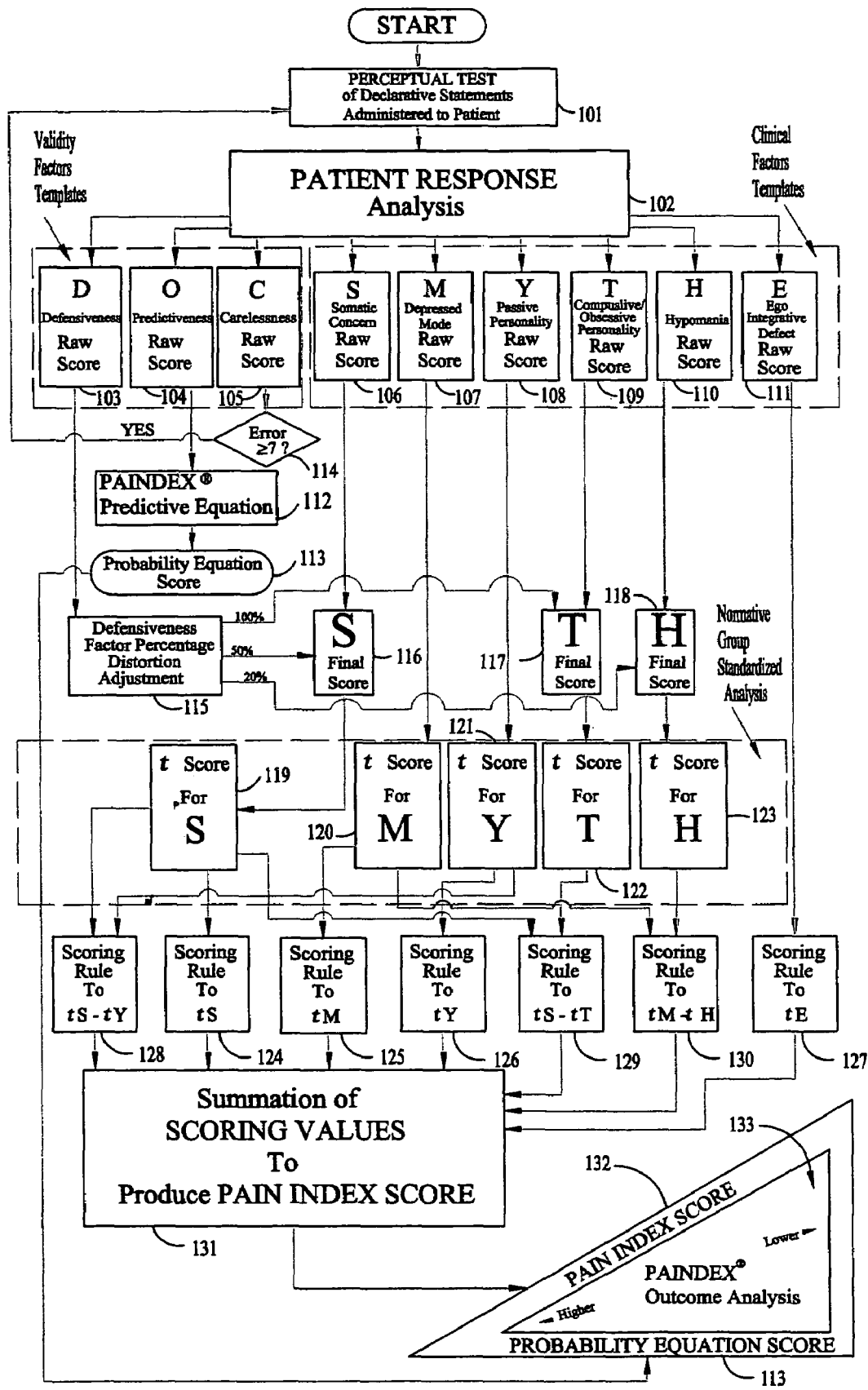
FIG. 1 Shows a procedural flow chart illustrating the preferred embodiment of a method for diagnosis of pain relief probability through medical treatment according to the present invention.

The present invention pertains to a method of diagnosing patients, with chronic pain, having somatization, in order to assess a probability of relief of such pain through medical or surgical treatment, by administering to a patient a self-reporting diagnostic test that identifies and quantifies a plurality of psychological and behavioral, clinical factors. Such clinical factors may affect treatment outcome for a patient sensitive to somatization, and have a bearing on a decision by a physician to operate or otherwise medically treat a patient, and on predicting whether problems could occur post-operatively or after treatment. Accordingly, the present invention method is a diagnostic assessment of the mind-body interface, thereby testing the perception to pain, and analyzing the impact of somatization, that may be utilized by surgeons to objectively assess clinical (psychological and behavioral) factors that might have a bearing on the decision to operate or medically treat a patient. The present invention provides the surgeon with an additional diagnostic test for an objective assessment of such factors. The present invention accomplishes these objectives by identifying and quantifying psychological and behavioral problems through the use of patient responses to declarative statements and by predicting the statistical probability of pain relief after treatment, particularly where pain symptoms do not correspond with physical findings and diagnostic studies.

The present invention method yields two independent predictive diagnostic values: a "Pain Index Score" and a "Probability Equation Score." The Pain Index Score and the Probability Equation Score are generated in the present invention by predictive algorithms derived from patient responses to the declarative statements included in a questionnaire, in the present embodiment of the invention, of one hundred ninety (190) declarative statements, to which the subject patient responds by either marking true or false on a response sheet. These one hundred ninety (190) declarative statements are used by the invention to determine which psychopathology and behavioral factors have a strong relation to surgical or treatment outcome for a patient, and were initially developed as part of the MMPI, the standard personality test in this field of art. The patient responses are divided into sets of three (3) validity factors and six (6) clinical factors and then evaluated to yield a graphic profile of factors that can be assessed statistically.

The Probability Equation Score is calculated utilizing a set of probability equations developed by the Inventor from clinical observations and marketed as the Paindex® Predictive Equation model. A personality correlation to pain relief has been determined through a logarithmic regression equation developed by the MMPI, as identified above. The Inventor has amended the MMPI testing procedure and the specific declarative statements thereto to better reflect his clinical observations and the goals of his method, to produce the Paindex® Predictive Equation for personality correlations to pain relief.

The Pain Index Score is calculated independently from six (6) clinical factor templates developed by the Inventor. The two independent predictive values, the Pain Index Score and the Probability Equation Score, are compared and reported to patient surgeons as the statistical probability of pain relief.

As illustrated first by a flowchart, FIG. 1, the method of the present invention consists, initially of a plurality of true/false declarative statement, or as a perceptual test 101 to be administered to and answered by the patient to predict the impact of somatization affecting a patient's pain perception prior to his receiving medical or surgical treatment. The declarative statements are set forth in a testing booklet, as potential descriptions of patient attitudes and feelings. The one hundred ninety (190) declarative statements published in the Paindex® Test Booklet, by Cortical Function Laboratory, Denver, Colo., collectively constitute the test 101, each declarative statement set forth corresponding to a response number in a response sheet, FIG. 2, in numerical sequence.

Figure 2:
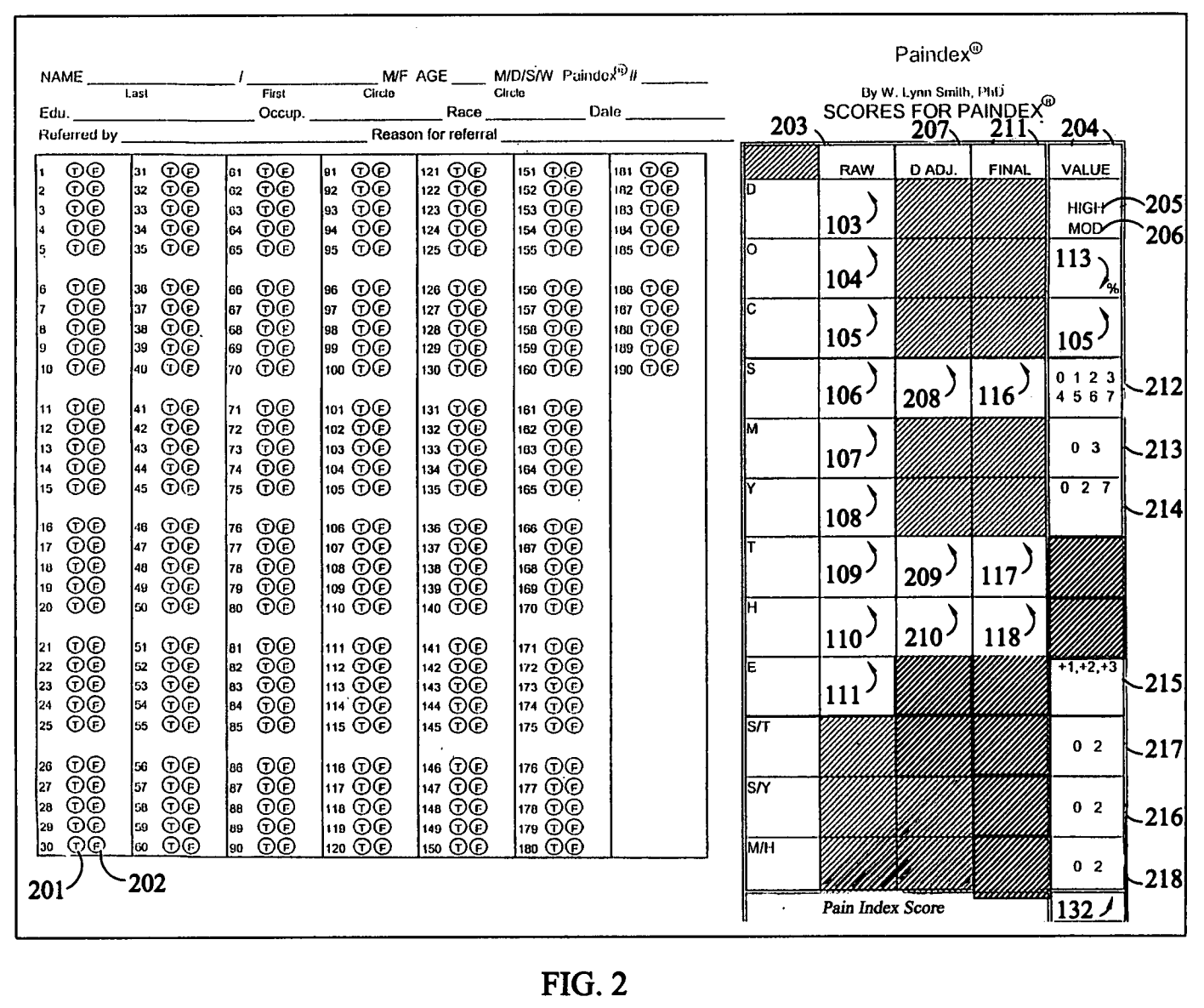

The patient, in initial instructions for taking the test 101 provided by the Inventor, is instructed to be honest and sincere in marking responses to each of the declarative statements. Each declarative statement is identified by its correlative number on the response sheet, FIG. 2, and each declarative statement number on the response sheet has, as shown in FIG. 2, a (T) for true 201 and a (F) for false 202, the desired response to be marked as directed by test 101 instructions provided by the Inventor. The patient is instructed to mark each response number as true 201 if a patient feels the declarative statement is descriptive of his attitude or feeling, or false 202 if he disagrees and feels that a particular declarative statement is not so descriptive. The patient is directed to use his first impression as the best response and to respond to every declaratory statement. There is no time limit for completing the responses to the declarative statements to test 101.

The test 101 is followed by an analysis and division of the patient's responses 102 into certain test validity factors (designated D 103, O 104 and C 105) and clinical factors (designated S 106, M 107, Y 108, T 109, H 110, and E 111). Two of the three validity factors as used in the present invention (D and C) are defined in the MMPI and further described in a standard reference in the field of art, Roger L. Greene, *The MMPI-2/MMPI: an interpretive manual*, Allyn and Bacon, Boston et. al. (1991), wherein the D (or defensiveness) and C (or carelessness) validity factors are identified as K and C, respectively, in Greene, pp. 37, 65–68 and 117–118. Each of the nine clinical factors as used in the present invention are defined in the MMPI, and further described in Greene, wherein the S (or somatic concern), M (or depressed mode), Y (or passive personality), T (or compulsive/obsessive personality), H (or hypomania), E (or ego integrative defect) clinical factors are identified as Hs, D, Hy, Pt, Mo and Es, respectively, in Greene, pp. 135–186.

The O (or predictiveness) validity factor, used as a standard factor in the industry and originally defined as the Owens Predictive Score$^{SM}$ by R. G. (Robert) Owens, Ph.D., psychologist, as referenced in Hamlin, Hitchcock and Hofmeister. Once the test 101 is completed, the Inventor (or other clinician administering the test 101 to the patient) applies each of nine separate scoring templates (FIGS. 3, 4 and 6–12) for tabulation and evaluation of the patient's responses. Each of these templates (FIGS. 3, 4 and 6–12) consist of a set of pre-selected declarative statement response profiles for the representative responses regarding the nine factors described above, the three (3) validity factors (D 103, O 104 and C 105) and the six (6) clinical factors (S 106, M 107, Y 108, T 109, H 110 and E 111).

The clinician uses each template (FIGS. 3, 4 and 6–12) to review patient test responses to the specific declarative statements corresponding to each of the nine (9) factors (D 103, O 104, C 105, S 106, M 107, Y 108, T 109, H 110 and E 111), by overlaying each template over the response sheet, FIG. 2, and counting the number of responses from the patient that identically correspond to the pre-selected responses contained on each template. The raw score for each of the factors, except C 105 (D 103, O 104, S 106, M 107, Y 108, T 109, H 110 and E 111), in the test 101, is based on the number of patient responses to the declarative statements set forth in FIG. 2 that correspond exactly with the pre-selected responses as indicated on the applicable factor template (FIGS. 3, 4 and 7–11) for each factor. The C 105 factor raw score is the number of patient responses that do not correspond to the pre-selected responses in the C template, FIG. 6, as further explained below.

The Inventor has set forth the declarative statements so that a "negative," or deviant, response to a declarative statement is a response that reflects an unhealthy mind or body condition. For example, a negative response to the test declarative statement: "My sleep is not sound or restful" would be "True" 201. A non-deviant, or healthy, response would be characterized as a positive response, "False" 202 in this example. The Inventor has formulated the declarative statement critical to an analysis of the six clinical factors, collectively constituting the patient response analysis 102.

Figure 3:
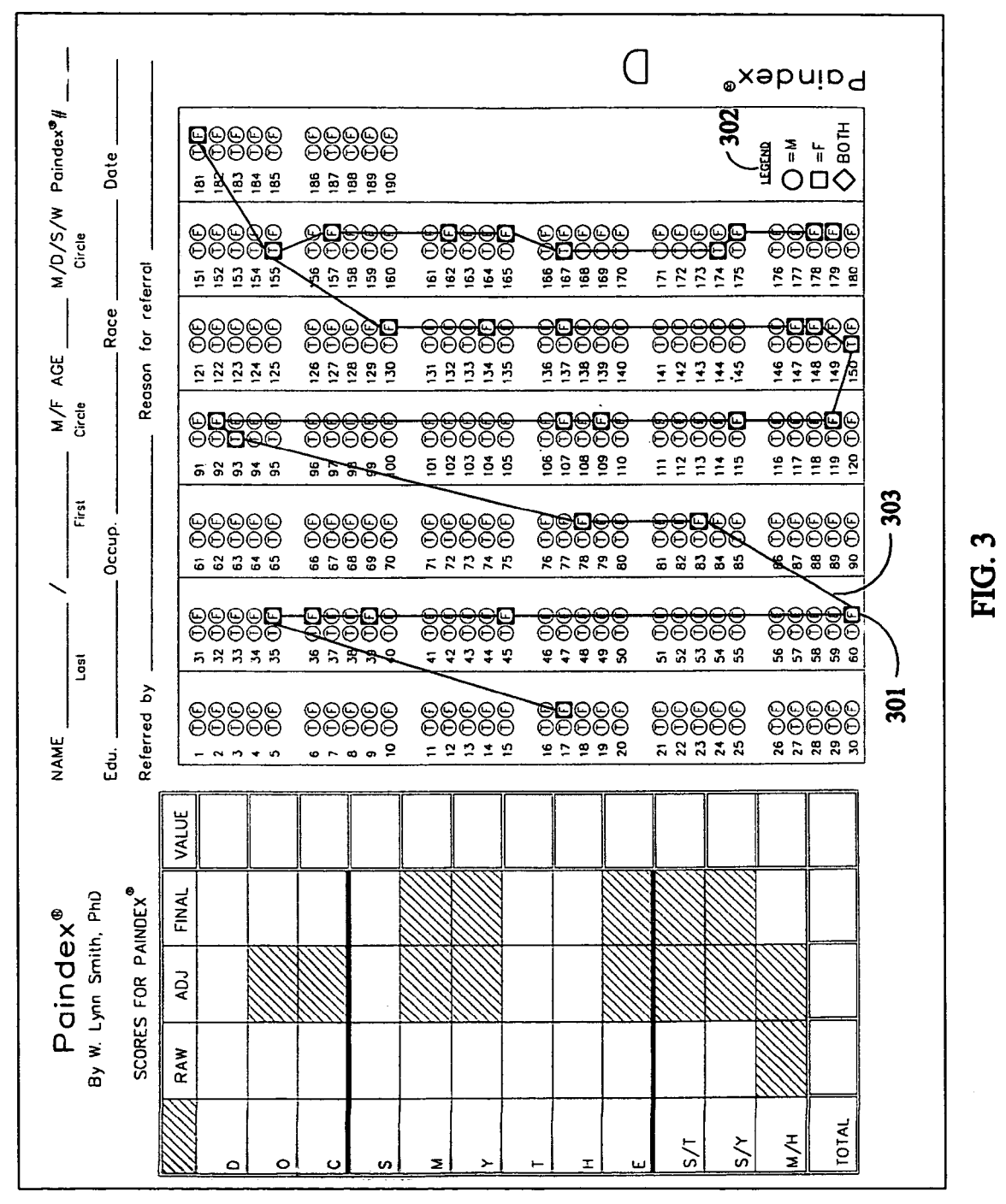

The first response template, FIG. 3, sets forth the pre-selected D 103 validity factor responses to thirty (30) certain declarative statements from those set forth in the test 101, as designed by the Inventor for the D 103 factor. The D 103 factor is measured to provide an adjustment to the response scores to the clinical factors, for defensiveness in the event that the patient taking the test 101 attempts, through his responses recorded in FIG. 2, to hide his true feelings or place himself in a "best possible light." The declarative statements constituting the D 103 factor are obtained from standard personality questions developed from the MMPI, and included in the test 101 as declarative statements for this particular factor.

The D template, FIG. 3, exhibits a response sheet 301 that marks certain pre-selected responses that correspond to the D 103 factor declarative statements. The D 103 raw score is recorded in FIG. 2 for the number of patient's responses in FIG. 2 to the declarative statements that correspond to the pre-selected responses in the D template, FIG. 3, for the same declarative statements. As noted by the legend on the D template 302, all of the responses apply equally to either gender taking the test. A solid line 303 connects all of the pre-selected responses in FIG. 3.

All responses by the patient to these particular D 103 declarative statements matching the pre-selected responses on the D template, FIG. 3, result in a point tallied for a resultant D 103 raw score. This D 103 raw score is recorded on the response sheet, FIG. 2, in the chart adjacent to the true/false response record, under the column labeled RAW 203. Reviewing FIG. 2 further, a general assessment by the clinician scoring the test 101 is made under the column labeled VALUE 204, to indicate whether a particular D 103 raw score is relatively high (column labeled HIGH 205) or moderate (column labeled MOD 206), based on overall clinical observations of a defensiveness trait.

Figure 4:
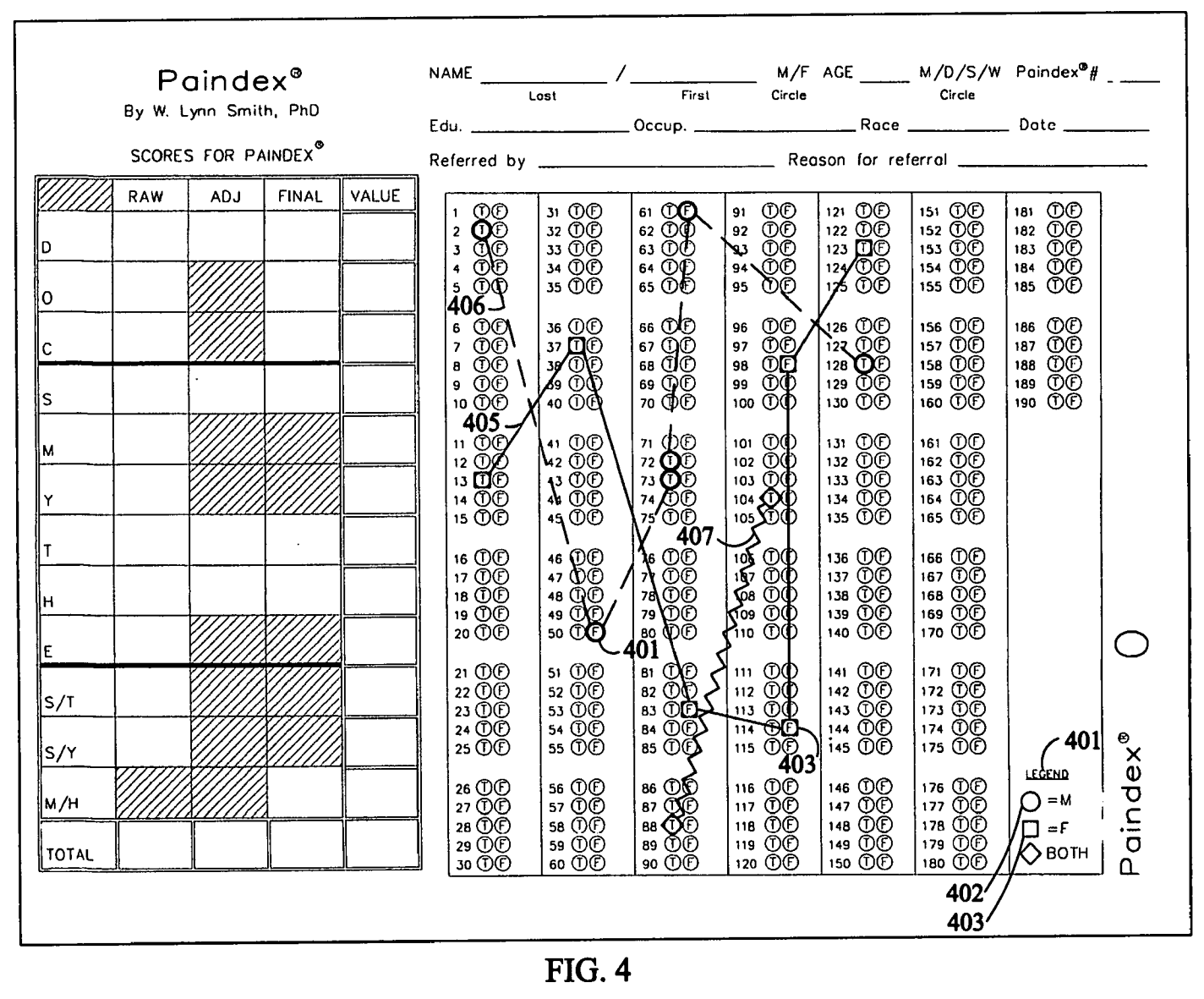

The second validity factor, O 104, on FIG. 1, the predictiveness validity factor, referred to as the Probability Equation Score 113 referenced above, predicts the probability of patient treatment success (separately for males and females) by an application of pre-selected declarative statement response scores, evaluated by the O template shown in FIG. 4, to certain percentages as developed by the Inventor and marketed under Paindex® as the Paindex® Predictive Equation 112. The Paindex® Predictive Equation model is outlined in FIG. 5. The O 104 raw score, is arrived at by counting the number of responses from the patient's test results in FIG. 2 that exactly correspond with the pre-selected responses on the O template illustrated in FIG. 4, for eight (8) specific declarative statements in the test 101, as identified in the O template by the symbols set forth in the Legend 401 therein.

There are six (6) specific declarative statements in the test 101 declarative statements identified by the O template, FIG. 4 Legend 401, six each for males 402 and six for females 403, with two declarative statements 404 shared by the genders, for a total of eight (8) declarative statements for each gender in FIG. 4 within the set of test 101 declarative statements. The gender-applicable set of O 104 factor responses are connected in the O template by a line according to patient gender (solid line for female 405, dashed line for male 406 and jagged line for the two shared declarative statements 407). The test 101 scores of male and female subjects are scored separately for the O 104 factor because the Inventor has found from clinical work that the O 104 factors correlated with pain relief are gender specific. The O 104 raw score is recorded on the scoring chart to the response sheet in FIG. 2 under RAW 203.

The probability equation score 113 is determined by applying the O 104 raw score to the Paindex® Predictive Equation 113 model set forth in FIG. 5. A percentage value is assessed based on the patient's O 104 raw score and the patient's gender, from either the eight (8) declarative statement scores for the Female Probabilities of Success 501 or the eight (8) declarative statement scores for the Male Probabilities of Success 502. The corresponding probability equation score 113, to the right of these Probabilities of Success in FIG. 5 is recorded on the response sheet, FIG. 2, under VALUE 204, for the O 104 factor probability equation score 113.

As set forth in FIG. 5 for the O 104 factor, the Male Probabilities of Success 502 percentage values to the Paindex® Predictive Equation 113 model have been "smoothed" (or adjusted) for better comparison of the male/female scales, due to observed gaps in a distribution of male clinical scores, to aid in comparisons of male and female O 104 raw scores.

The O 104 factor raw score is one of two independent values in the present Invention assessing probability of patient treatment success. The lower the O 104 factor raw score, the lower the probability equation percentage, utilizing the Paindex® Predictive Equation in FIG. 5, and the stronger the indication that the patient may experience a poor treatment outcome. This probability equation score 113 percentage is preserved on the response sheet, FIG. 2, and used subsequently in the method to the present invention to verify and support a commensurate "Paindex® Score" for predicting a successful treatment outcome aimed at pain relief.

The third validity factor, C 105, and the C 105 raw score, represent a relative measure of testing "carelessness" by the patient; where, as examples, the patient is: not taking the test 101 seriously, not reading the test 101 declarative statements carefully, having test 101 language or understanding problems, poorly motivated to take the test 101, having problems with honesty or sincerity, randomly responding to test 101 declarative statements without actually reviewing them; or having other, related psychological issues. The C 105 factor raw score is considered with, or factored into, subsequent clinical raw scores (S 106, M 107, Y 108, T 109, H 110 and E 111), as well as the D 103 and O 104 raw scores, to diminish the effect of unrepresentative scoring factors in the test 101 through conscious or subconscious careless efforts of the test 101 taking patient. As such, the C factor raw score 105 measures inconsistencies, or "errors" 114, in the responses by the patient (intended or unintended) to certain coupled declarative statements, pre-selected by the Inventor from the test 101 declarative statements, when any of the coupled responses from the patient are inherently contradictory.

Figure 6:
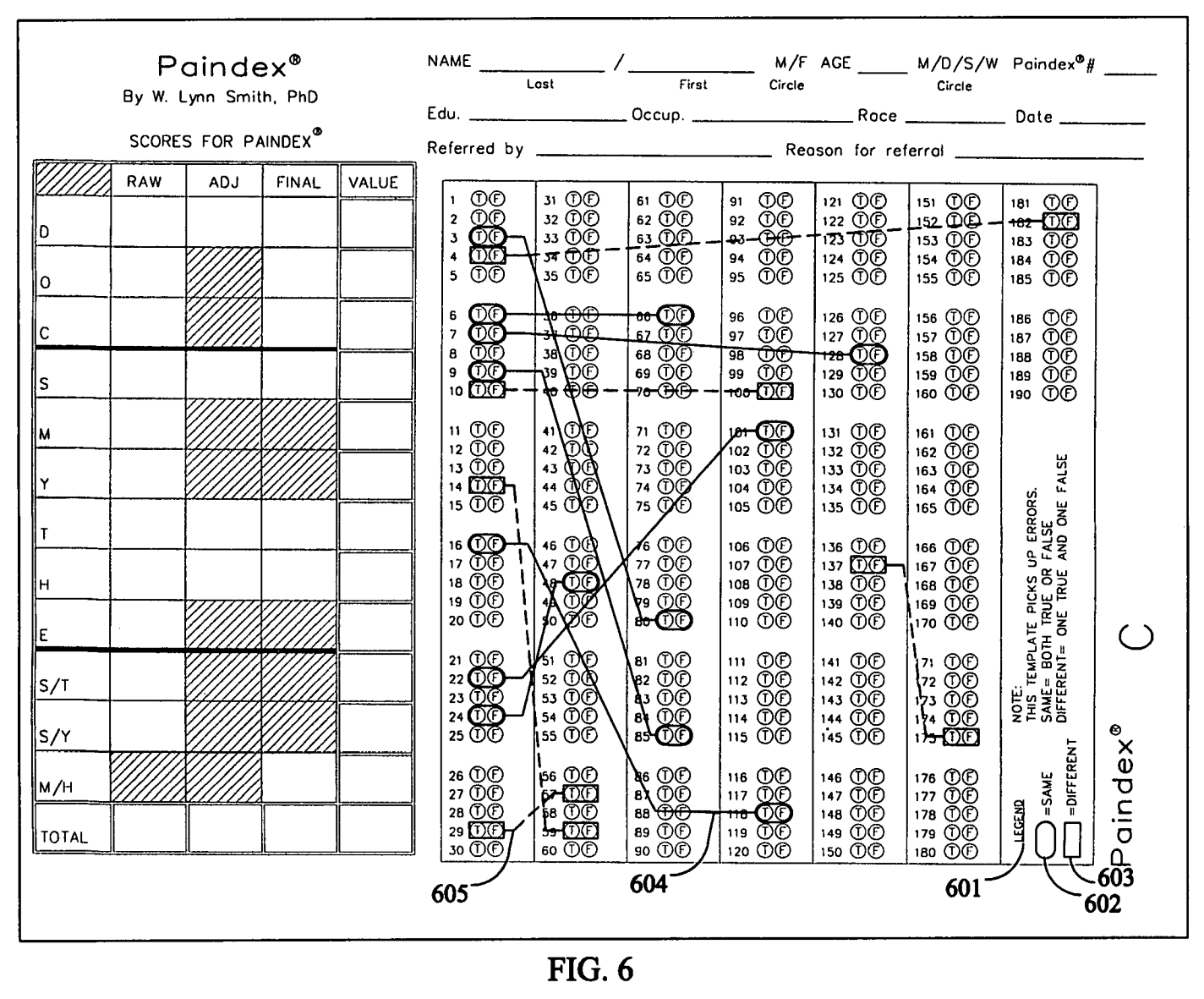

There are twenty-four (24) such coupled declarative statements in the test 101 identified in the C template in FIG. 6, identified by the Legend 601 to the C template, fourteen (14) of which declarative statements would generate a consistent (or "same") response in their 10 (ten) coupled declarative statements from an inattentive patient (one making inconsistent responses) and an opposite (or "different") response in the coupled declarative statements from an attentive patient (one making consistent responses) taking the test 101. The C template, FIG. 6, exhibits fourteen (14) coupled declarative statements pre-selected by the Inventor from the test 101 Items, for which the patient's responses to are required to be the same (both true or both false) (responses 602 in oblong geometric features connected by solid lines 604), and the ten (10) coupled declarative statements pre-selected by the Inventor from the test 101 Items, for which the patient's responses are required to be different (either true or false) (responses 603 in rectangles connected by dashed lines 605). The C 105 raw score is arrived at by counting the number of responses from the patient's test 101 results in FIG. 2 that do not correspond with the pre-selected responses for the twenty-four (24) coupled declarative statements on the C template as illustrated in FIG. 6.

The declarative statements utilized for the C 105 factor raw score (recorded in FIG. 2) are derived from the MMPI. A relatively high C 105 factor raw score reflects patient carelessness in taking the test 101. A C 105 raw score of seven (7) or more (≧7) is determined by the Inventor to invalidate the test 101 because it represents a potential for an unacceptably high number of inattentive responses to the test by a patient. In essence, the C 105 factor is a carelessness check 114 to alert the clinician as to whether there is potential for this factor to impact the validity of the test 101, and a need for the patient to retake the test 101.

The C template, FIG. 6, for scoring the declarative statements producing the C raw score 105 is the same for both males and females. The C raw score 105 is recorded in FIG. 2, under RAW 203 and VALUE 204, respectively.

Patient responses to the D 103 factor and C 105 factor declarative statements are used to analyze the inherent representativeness of all of the patient's test 101 responses to all of the declarative statements in the test 101. For example, a high D 103 factor raw score can distort the test findings where the patient is trying to present, in his own mind, as "good" a picture or highly conventional picture, as possible, thereby attempting to hide or mask his true feelings. The higher the D 103 factor or C 105 factor raw scores, the more probable it is that the test 101 has an inherent validity problem.

The six (6) clinical factor raw scores (S 106, M 107, Y 108, T 109, H 110 and E 111) from the test 101, as set forth in FIG. 1, reveal certain patient personality characteristics. These personality clinical factors do not identify a particular personality; rather they are measured to indicate a patient's perception of pain based on personality factors and how his personality affects how he may handle such pain. As such, the present invention of the Inventor is not a personality test.

As to the individual clinical factors, S 106 represents somatic concern; M 107 represents a depressed mode; Y 108 represents a passive personality; T 109 represents a compulsive/obsessive personality; H 110 represents hypomania (as in the case of an up-and-down personality of a cycloid individual who denies either having, or the extent of, emotional problems); and E 111 represents an ego integrative defect (a weak ego).

The final clinical factor, E 111, is a critical factor in predicting somatization and treatment outcome for patients in the present invention because the Inventor has found it to be a highly sensitive indicator for detecting somatization disorders. The lower the E 111 raw score, the greater the probability exists that a patient has an ego integrative defect or that his ego integration is seriously flawed, to the extent that the patient may have a pre-psychotic personality, dramatically affecting the probability of a successful treatment outcome for the relief of pain. Therefore, the E 111 factor is a more influential factor among the six (6) clinical factors (S 106, M 107, Y 108, T 109, H 110 and E 111) in the test 101.

Figure 7:
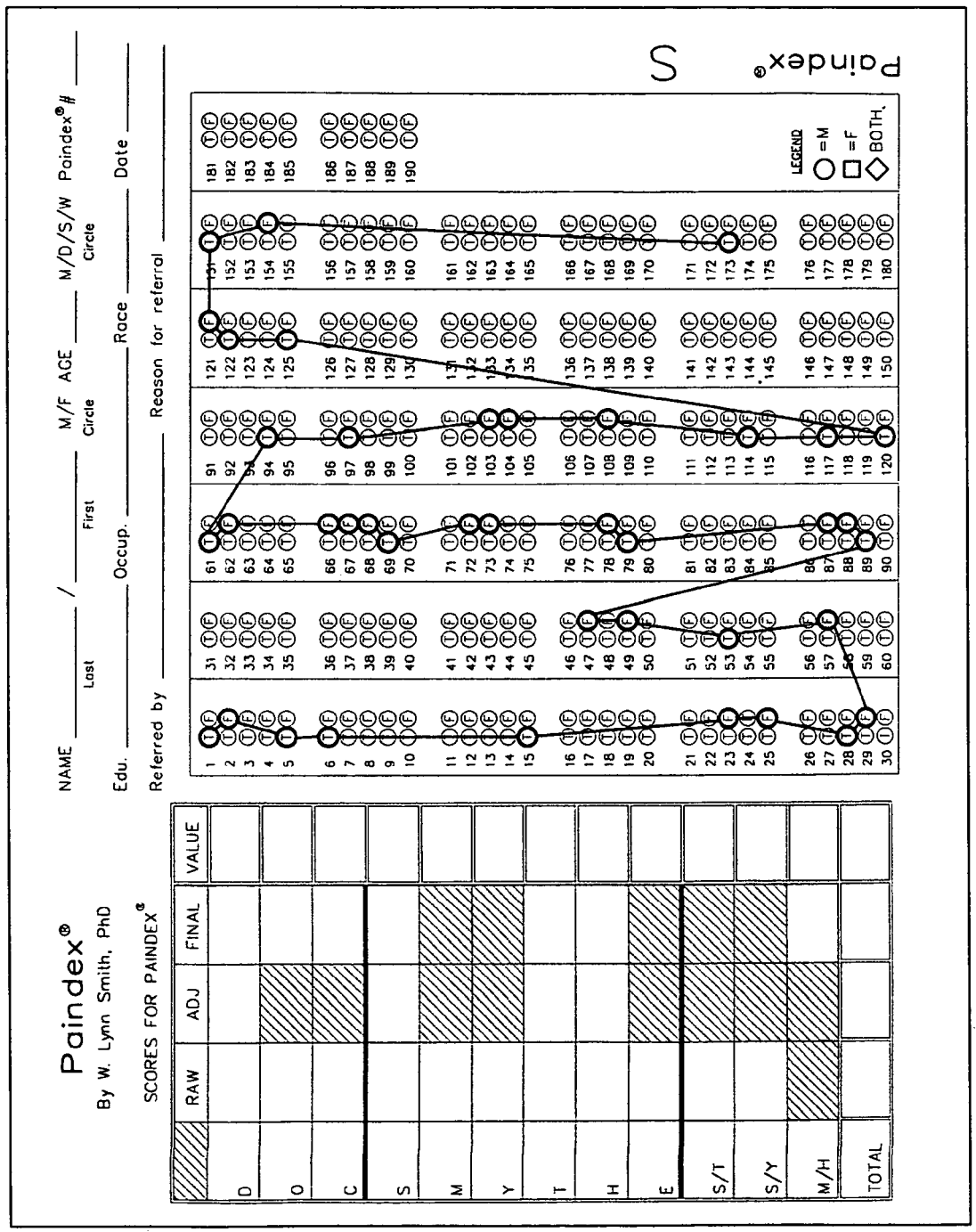
FIG. 7 Shows a response template to score the patient's "S" (somatic concern) clinical factor responses.
Figure 8:
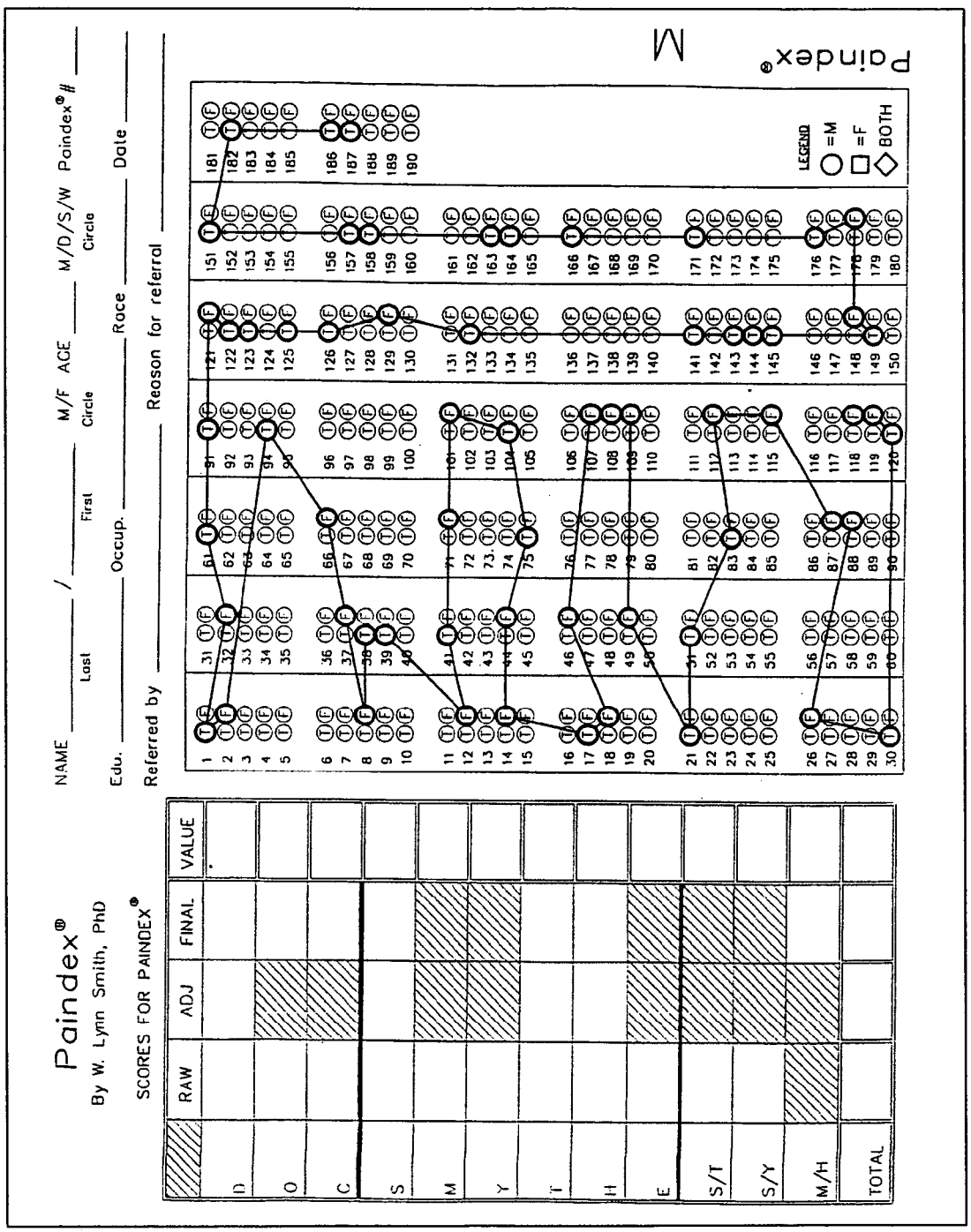
FIG. 8 Shows a response template to score the patient's "M" (depressed mode) clinical factor responses.
Figure 9:
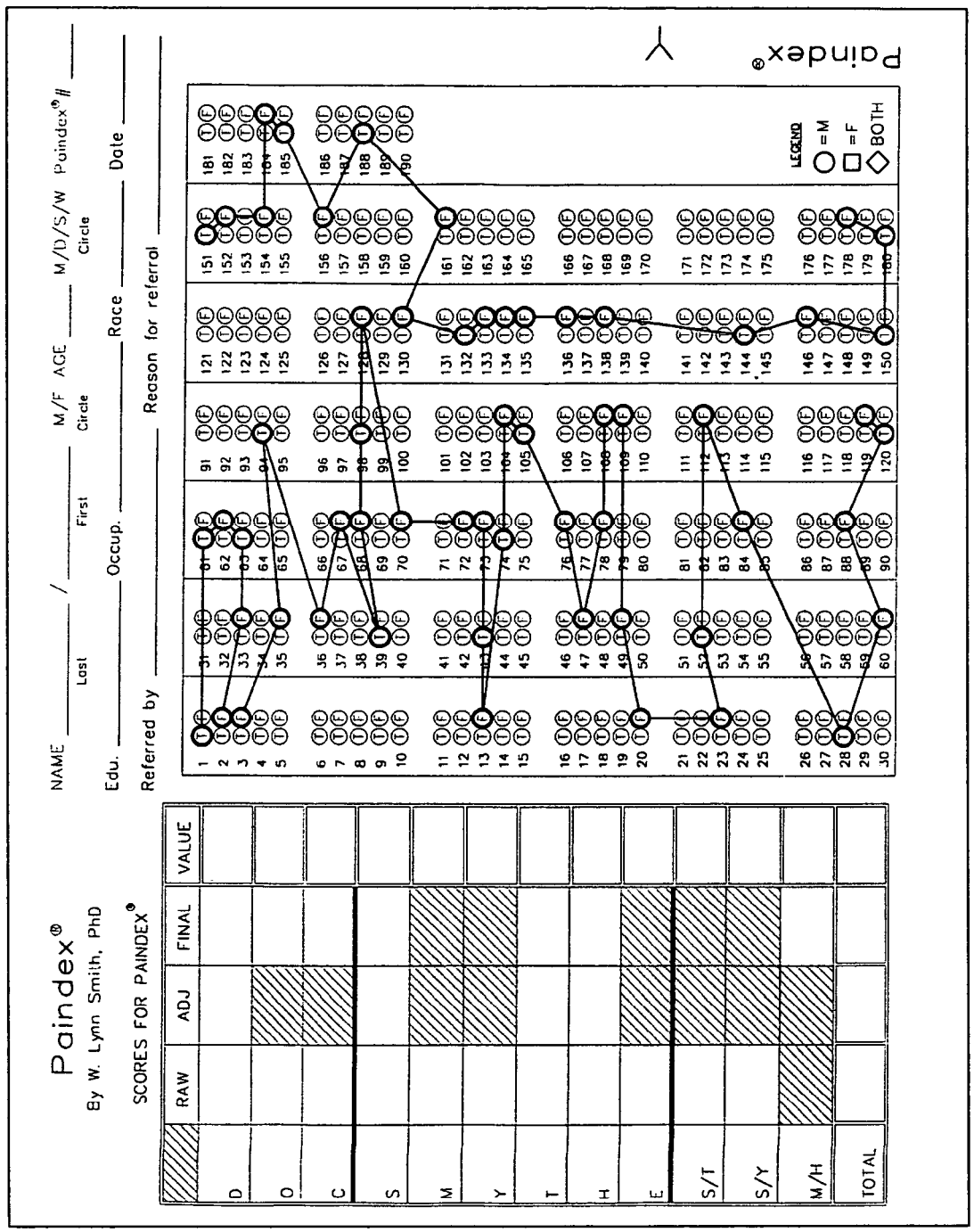
FIG. 9 Shows a response template to record the patient's "Y" (passive personality) clinical factor responses.
Figure 10:
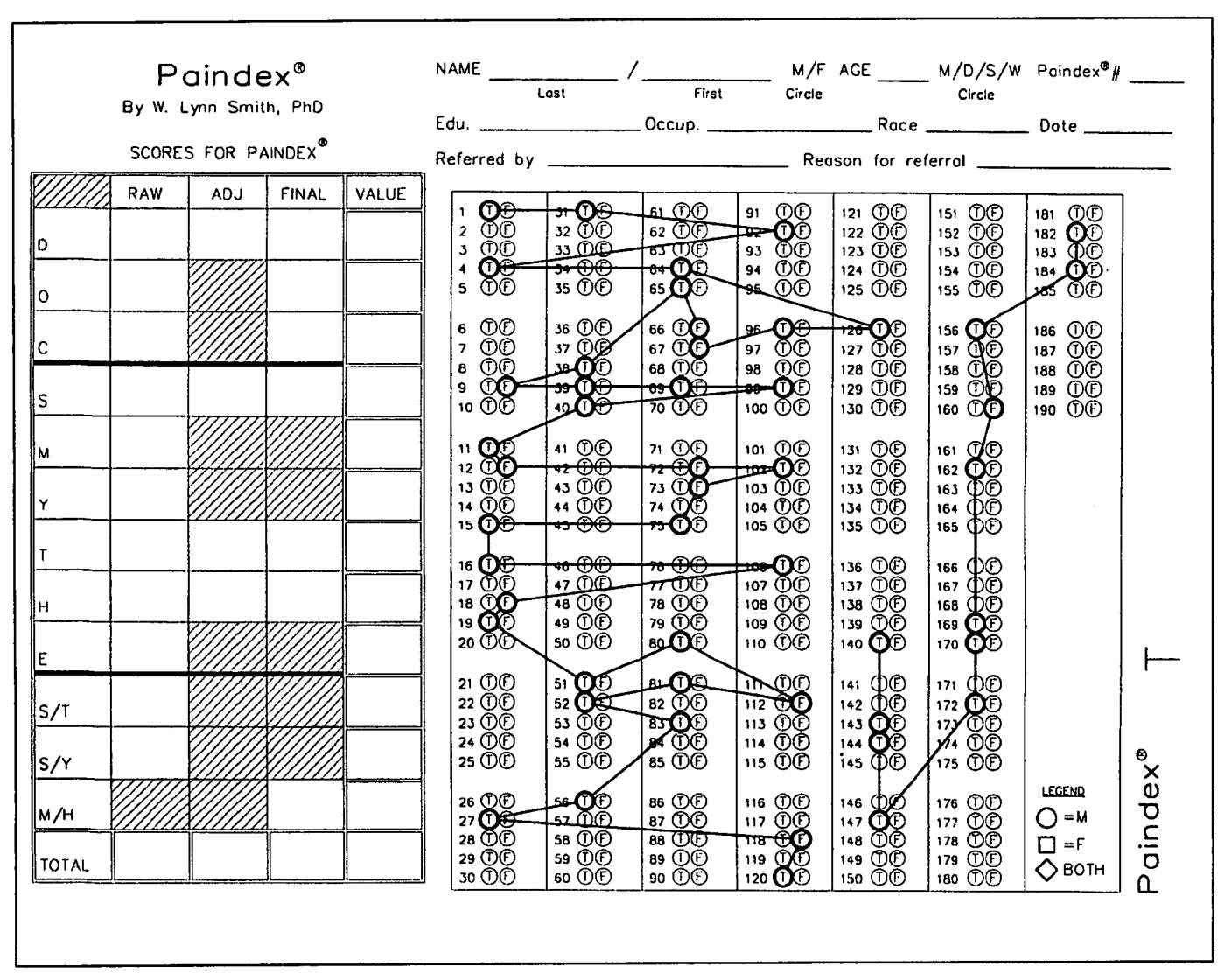
Figure 11:
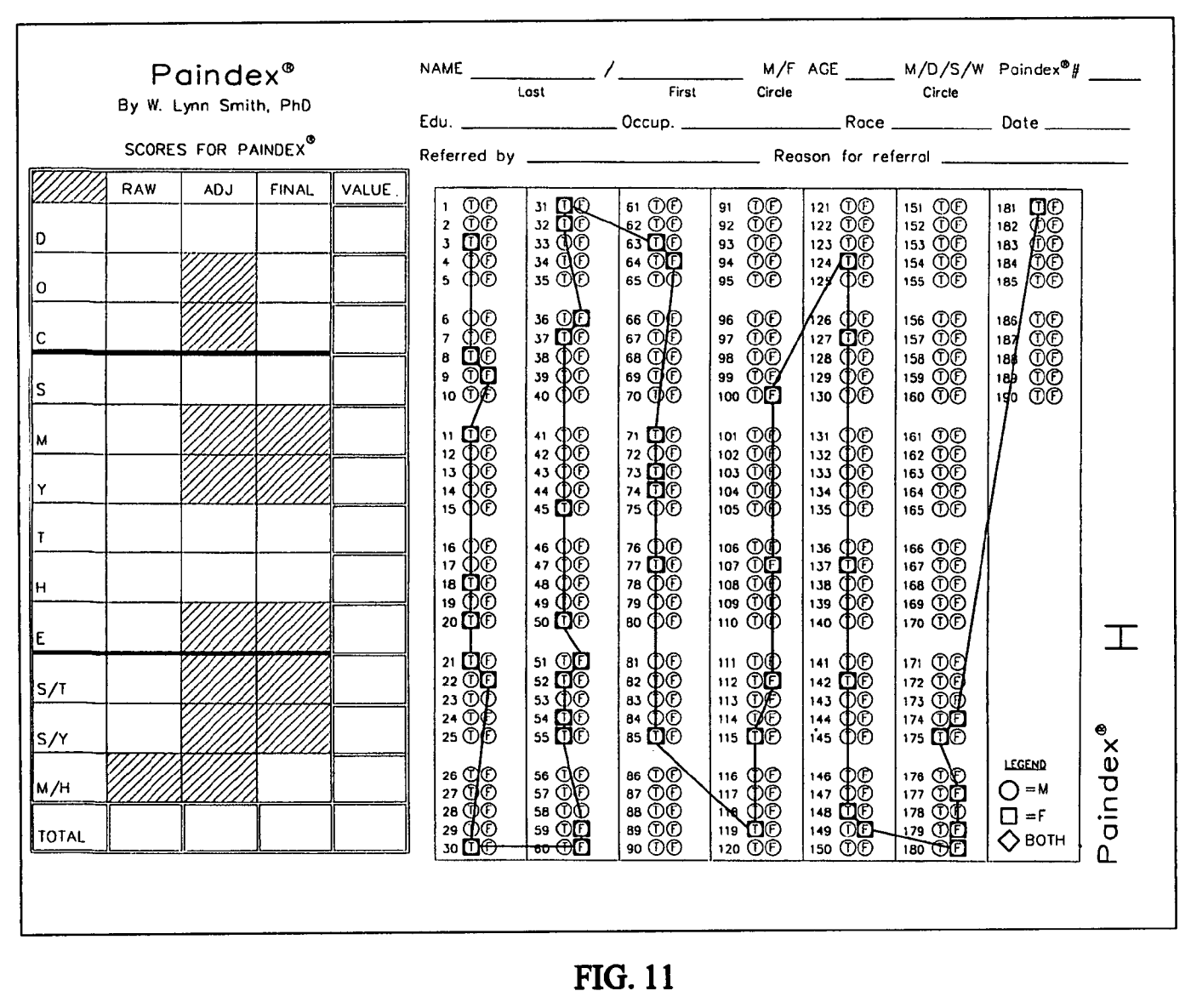
Figure 12:
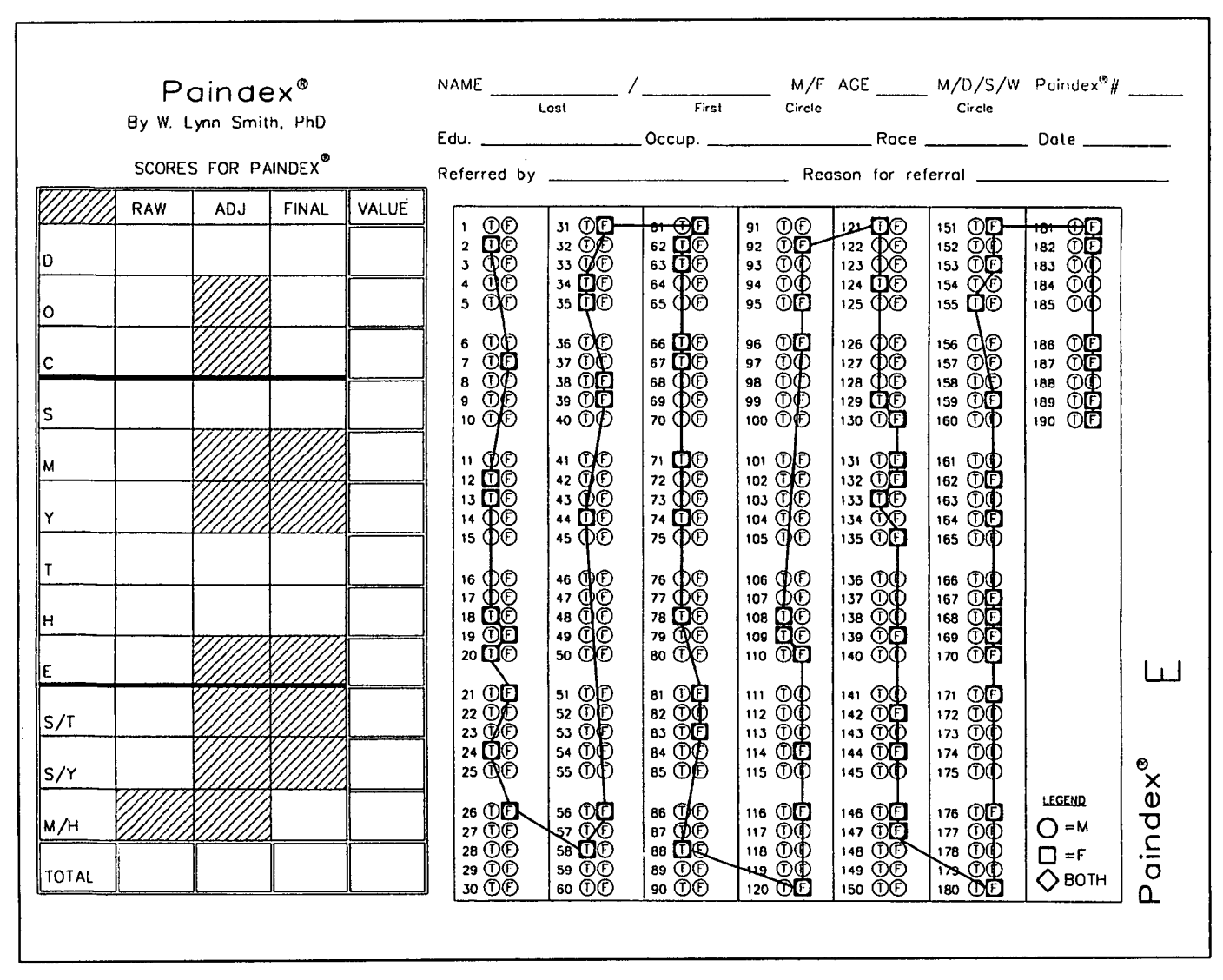

Raw scores, recorded in FIG. 2 under RAW 203 of the number of responses to the specific test 101 declarative statements for each of the six (6) clinical factors (S 106, M 107, Y 108, T 109, H 110 and E 111) are calculated in the same manner as for the three (3) validity factors (D 103, O 104 and C 105) set forth above, utilizing the applicable template for each respective clinical factor (FIG. 7 for S 106, FIG. 8 for M 107, FIG. 9 for Y 108, FIG. 10 for T 109, FIG. 11 for H 110 and FIG. 12 for E 111). The required responses to the test 101 declarative statements for each of templates FIGS. 7 through 12 are gender neutral. The raw scores for the six (6) clinical factors (S 106 raw score, M 107 raw score, Y 108 raw score, T 109 raw score, H 110 raw score and E 111 raw score) are recorded under RAW 203 in FIG. 2. The set of required responses for each of templates FIGS. 7 through 12 are connected by solid lines for ease of score calculation.

Once the raw scores for all nine (9) factors (D 103 raw score, O 104 raw score, C 105 raw score, S 106 raw score, M 107 raw score, Y 108 raw score, T 109 raw score, H 110 raw score and E 111 raw score) have been determined and recorded under RAW 203, in FIG. 2, an adjustment by a percentage of the defensiveness factor raw score is made to the S 106 raw score, to the T 109 raw score and to the H 110 raw score. These three (3) factor raw scores are adjusted to offset any distortion to the test 101 responses where the patient is attempting to hide or mask his true feelings, as identified by the D 103 factor raw score described above. A defensiveness distortion adjustment 115, in FIG. 1, an applicable percentage of the defensiveness factor raw score, is applied to the S 106 raw score, T 109 raw score and H 110 raw score to adjust for any distortion in the findings of these three (3) clinical factors, which clinical factors are found by the Inventor to be susceptible to the D 103 factor defensiveness phenomenon. The M 107, Y 108 and E 111 raw scores are not adjusted because clinical observations by the Inventor show low potential for any distortion by the D 103 factor to scores for those clinical factors. The defensiveness distortion adjustment is calculated from the D 103 raw score, by an amount of either 1.00 (100%), 0.5 (50%) or 0.2 (20%) of the D 103 raw score. The calculated amount of the respective defensiveness distortion adjustments for the S 106 raw score, the T 109 raw score and the H 110 raw score in the patients's test 101 are set forth in FIG. 2 under a D ADJ. 207 column. The S 106 factor raw score in a patient's test 101 is adjusted upward by adding fifty percent (50%) of the D 103 raw score to the S 106 raw score, by an S adjustment 208 amount tabulated on FIG. 2. The T 109 factor raw score is adjusted upward by adding one hundred percent (100%) of the D 103 raw score to the T 109 raw score, by a T adjustment 209 amount tabulated on FIG. 2. Finally, the H 110 factor raw score is adjusted upward by adding twenty percent (20%) of the D 103 raw score to the H 110 raw score, by an H adjustment 210 amount tabulated on FIG. 2. Each of the three (3) adjustment scores recorded under D. ADJ 207 in FIG. 2 are added to their applicable S 106, T 109 and H 110 raw scores, under RAW 203 as set forth in FIG. 2, to calculate "final scores" for each of these three (3) clinical factors. The final scores are recorded under a FINAL 211 column in FIG. 2 (for a final S score 116, for a final T score 117 and for a final H score 118). The raw score, the adjustment scores and the resultant final scores, if any, for each clinical factor are recorded on the response sheet in FIG. 2, under RAW 203, D ADJ. 207 and FINAL 211, respectively, in FIG. 1 and the FIG. 2 response sheet (S 116, M 107, Y 108, T 117, H 118 and E 111).

Figure 13:
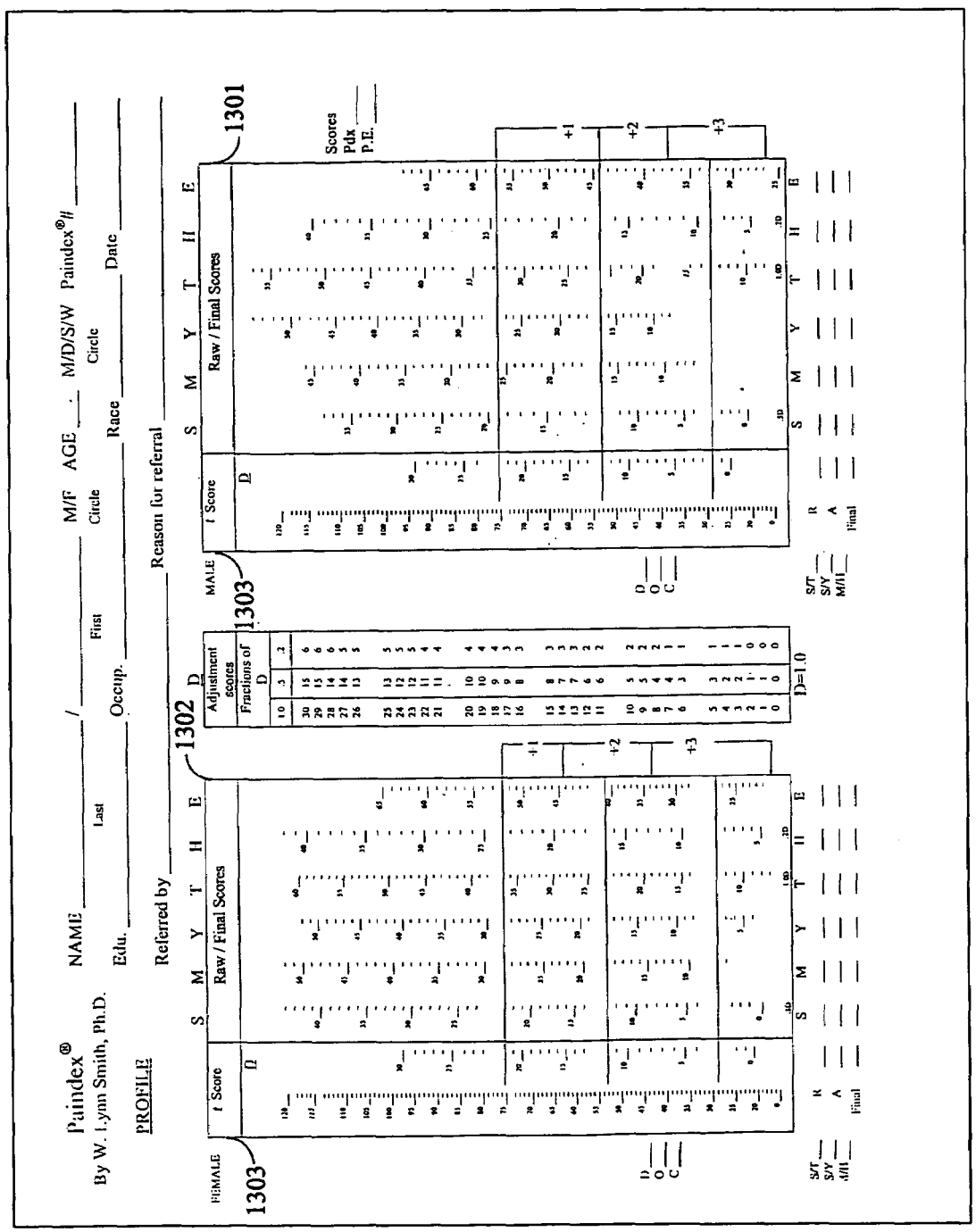
FIG. 13 Shows a Paindex® Profile, of gender-appropriate score standardizing scales for translating clinical factors into standard, or t, scores for a particular patient.

Raw or final scores for each of the clinical factors (adjusted or unadjusted raw scores, as applicable), except for E 111, are then translated into standardized, or "t", scores (shown in FIG. 1 as t score for S 119, t score for M 120, t score for Y 121, t score for T 122 and t score for H 123), for comparisons, ratios and further evaluation, utilizing FIG. 13, a Paindex® Profile of gender-appropriate score standardizing graphs for the particular patient. A standard t score determined for each clinical factor score, excluding E 111, normalizes the impact of each clinical factor score to each other score, allowing a clinician to compare each of the clinical scores to other clinical scores for the same or different patients and to add all of the t values together in order to assess each patient with one standardized or composite score.

A linear t score analysis was developed by MMPI as a formula for direct comparison of personality factors. A t score for clinical factor scores enables a clinician to compare patients' clinical scores with each other, by first showing how a particular patient scored compared to a "group of normals" on whom the MMPI was standardized (see Roger L. Greene, *The MMPI-2/MMPI: an Interpretive Manual*, pp. 37–38). The normals are those patients for whom clinical observations have determined a standard score linear curve for any particular clinical factor, a mathematically equated mean for that factor and a standard deviation from the mean for the factor scores of deviations off the standard score linear curve. The t scores are termed linear t scores because they are linear transformations of the raw scores that maintain the underlying distributions of the raw scores. Certain clinical factor combinations and scale configurations of the clinical factor raw and final scores (as graphed in FIG. 13 for S 116, M 107, Y 108, T 117 and H 118), used in this field were developed by Smith and Duerksen in 1979, W. Lynn Smith and Donald L. Duerksen, "Personality and the Relief of Chronic Pain: Predicting Surgical Outcome," Clinical Neuropsychology, 3$^{rd}$ Qtr. (1979), pp. 35–38.

By utilizing the profiles shown in FIG. 13 and by graphing FINAL 211 scores and RAW 203 scores for each clinical factor, respectively, and establishing t scores for each clinical factor (converting such adjusted and unadjusted scores to t scores), and by knowing mean t scores among normals for the same clinical factors, a clinician can determine a relative deviation and an interpretive importance of the FIG. 13 scales and clinical factor t scores to a particular patient.

The clinical factor FINAL 211 scores and RAW 203 scores for factors S 116, M 107, Y 108, T 117 and H 118, determined above, are each converted to their respective t scores through mathematical adjustments. Utilizing the t score analysis of factor scales set forth in FIG. 13, the clinician establishes a t score for each of the five (5) factors, by, first, plotting each of the five (5) clinical scores in the gender-appropriate profile entitled RAW/FINAL SCORE (a male patient profile 1301 or a female patient profile 1302) and, second, reading laterally across FIG. 13 from each RAW/FINAL SCORE for each of the five (5) factor scores (for example, those plotted in the male patient profile 1301) recorded for each of the clinical factors (S, M, Y, T and H), to a t score scale 1303 on the left side of each of the patient-appropriate gender profiles, male 1301 or female 1302.

The RAW/FINAL SCORES profiles for male patients 1301 and female patients 1302 and the t score scale 1303 scales in the present invention in FIG. 13 are provided so that clinicians may make direct observations, without performing any mathematical equations, to convert in FIG. 2, RAW 203 or FINAL 211 scores to t scores 1303. Individual clinical factor RAW/FINAL SCORE profile scales 1301 in FIG. 13 are staggered, or offset vertically, with respect to each other and with respect to the t score scale 1403 to provide the clinician with a direct method of establishing the relationship between the patient's test 111 scores (his raw or final S 116, M 107, Y 108, T 117 and H 118 scores) and to establish resultant t score for S 119, t score for M 120, t score for Y 121, t score for T 122 and t score for H 123.

Through clinical observations and linear equations, the Inventor has determined mean t scores applicable to each of five (5) clinical factors: S 116, M 107, Y 108, T 117 and H 118, including a set mean, or baseline, score for a clinical factor normative group, as observed in clinical studies, and a standard deviation above each norm, in order for the clinician to calculate a standard deviation point score, or "index point" (from Smith and Duerksen, Id.) for each patient. The present invention includes, in FIG. 14 entitled PAINDEX® SCORING VALUES, a set of scoring rules or a group of equations to be applied: to the t Score for S 119, or "tS" 124, to the t Score for M 120, or "tM" 125, to the t Score for Y 121, or "tY" 126 and to E 127 from the E raw score 111. The scoring rules set forth in FIG. 14 provide a means in the present invention to quantify a patient's t score deviations from the norm for clinical factors S 106, M 107 and Y 108.

Therefore, pursuant to FIG. 14 under the Scoring Rule for tS 124, in FIG. 2 for each 5 points that the tS score is greater than a mean score of 55, one (1) point is tabulated under VALUE 204, a total to which calculates a number of standard deviations above the normative group mean for an S Scoring Value 212. FIG. 2 anticipates under the Scoring Rule for tS 124 that a number of standard deviations tabulated for the S Scoring Value 212 will fall between zero (0) and seven (7). Determined in the same manner, a VALUE 204 for the other three (3) clinical factor Scoring Values, an M Scoring Value 213 and a Y Scoring Value 214, as well as an E Scoring Value 215, calculated from the E 111 raw score under the Scoring Rule to E 127, are entered in FIG. 2.

For clinical factor E 111, the present Invention utilizes the E 111 raw score and not a t standardizing component. The Inventor has developed separate scoring standard deviation numbers derived through clinical observations in relationship to the raw E 111 clinical factor. The Scoring Rule to E 127 set forth in FIG. 14 indicates that for a range of male E raw scores, there are applicable standard deviations above the normative group, recorded as E Scoring Value 215 under VALUE 204 in FIG. 2.

FIG. 14 also provides a set of scoring rules for numerical relationships to particular pairs of t scores: a scoring rule to tS-tY 128, a scoring rule to tS-tT 129, and a scoring rule to tM-tH 130. The scoring rules set forth in FIG. 14 provide a means in the present invention to quantify a patient's t score deviations from the norm with regard to comparisons of particular combinations of clinical factors: S 106 to Y 108, S 106 to T 109 and M 107 to H 110.

To measure the impact of anxiety in a patient, the tY 121 score is utilized in numerical relationship with the tS score 119 to calculate a standard deviation under the Scoring Rule to tS-tY 128, utilizing the FIG. 14 scoring rules 128 for tS-tY. From observations made by the Inventor in clinical research, patients may exhibit unique traits of anxiety within the mind in comparison with anxiety within the body. Pursuant to FIG. 14 Scoring Rule for tS-tY 128, where the tS score is equal to or greater than tY, a standard deviation of 2 above the normative group mean, or "S/Y" Scoring Value 216, is chosen under VALUE 204 in FIG. 2.

For the T 109 and H 110 clinical factors, no direct standard t scores are used alone in the present invention. Thus, no T Scoring Value or H Scoring Value is entered in FIG. 2 under VALUE 204. The Inventor utilizes the t scores from these two (2) clinical factors in numerical relationship with other clinical factor t scores to determine Scoring Values entered under Value 204 for additional comparisons (S/T 217 and M/H 218). A S/T Value 217 has been found clinically to be an important indicator of a direction for patient fear, toward mind or body. Pursuant to FIG. 14 Scoring Rule for tS-tT 129, where the tS score is greater than the tT score by eleven (11) or more points, a S/T Scoring Value 217 of two (2) standard deviations above the normative group mean is chosen under VALUE 204 in FIG. 2.

As mentioned, the H 110 factor is utilized in numerical relationship with the M 107 factor for a comparison, the M/H Scoring Value 218, which the Inventor has found clinically to be an indicator of elements or types of patient mood, either depression or elation when at relatively high levels, or an indicator of patient self esteem. Pursuant to FIG. 14 Scoring Rule for tM-tH 130, where the tM score is greater than the tH score by six (6) or more points a M/H Scoring Value 218 of 2 standard deviations above the normative group mean is chosen and recorded under VALUE 204 in FIG. 2.

Figure 15:
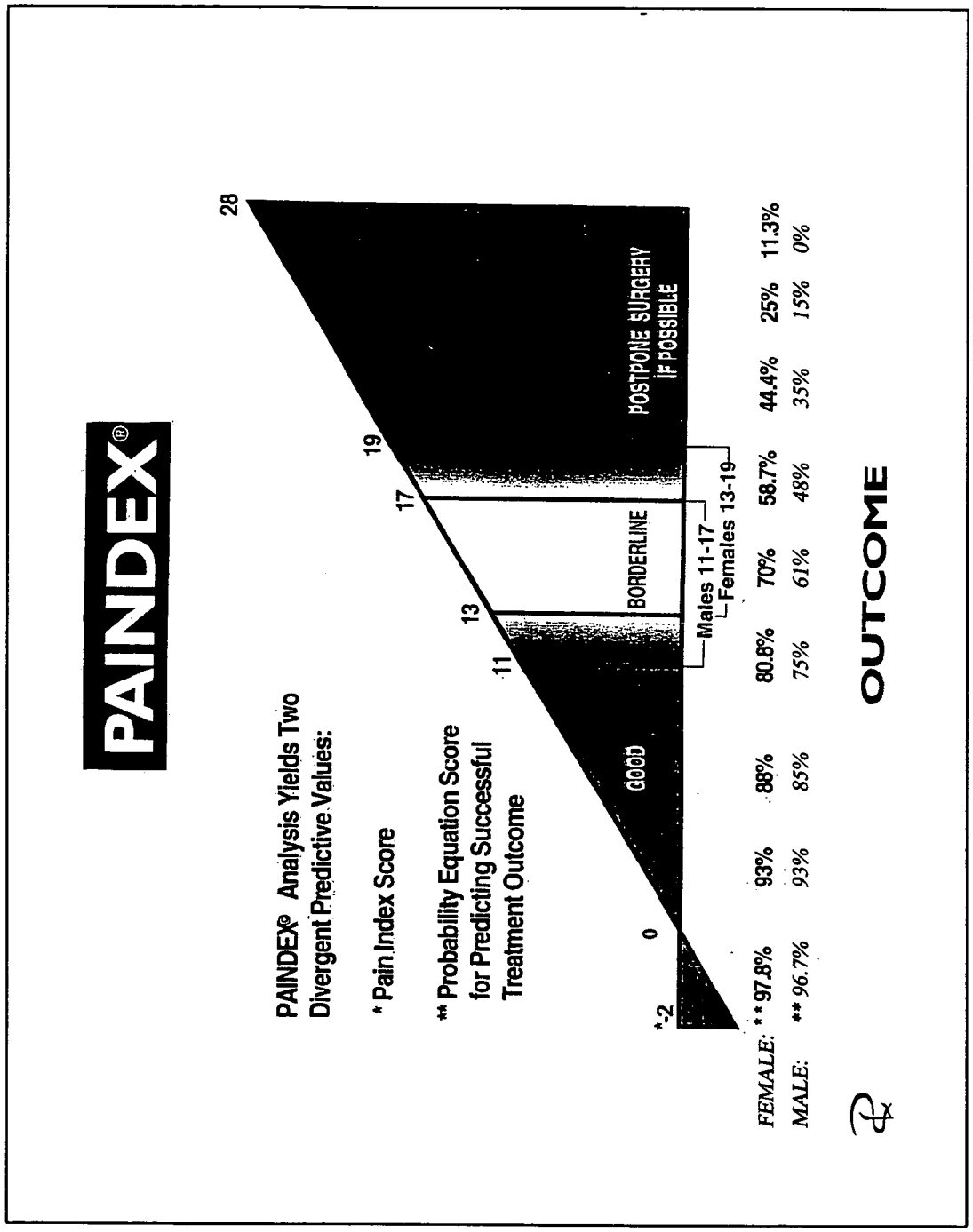
FIG. 15 Shows a graph of pain index scores and the probability equation scores to provide a prediction of a probability of pain relief.

The summation of all of the standard deviation Scoring Values 131 determined by the Scoring Rules set forth in FIG. 14; and recorded in FIG. 2 under VALUE 204: S 212, M 213, Y 214, E 215, S/T 217, S/Y 216 and M/H 218; produces a total points of standard deviation, or a single Pain Index Score 132. A Paindex® Outcome Analysis 133 graph, shown in FIG. 15, is a plot of the two (2) independently determined outcome predictive values to the present invention, the Pain Index Score 132 and the Probability Equation Score 113. The Paindex® Outcome Analysis 133 sets forth a comparative analysis of these two non-parallel, divergent predictive values for this Invention as a forecast of the interrelationships of the two values. Clinical observations of actual outcomes of patients who have been administered the Invention confirm the accuracy of these two predictive values and the internal validity of the present inventive method. The Pain Index Score 132 and the Probability Equation Score 113, as graphed and depicted in FIG. 15, diagnose a presence or absence of somatization in patients and provide a prediction of a probability of pain relief in approximately ninety-five percent (95±%) of patient cases. The present Invention, therefore, predicts within a high percentage of reliability, high degrees of somatization in patients having a poor probability of medical procedure outcomes, and low degrees of somatization in patents with good predictions of outcome.

An alternative embodiment of the present invention raises the E Scoring Value 215 from the Scoring Rule to E 127 to increase predictability when the patient's testing needs to be more focused on an ego-integrative-defect factor, measuring weak egos. In addition to the preferred embodiment, the clinical factors to the present invention may be alternatively arrayed for evaluating athletic injuries, selecting athletes for competition or evaluating pain complaints at issue in litigation.

Having thus described in detail a preferred selection of embodiments of the present invention, it is to be appreciated and will be apparent to those skilled in the art that many physical changes could be made in the method of the present invention without altering the invention, concepts and principles embodied therein. The present invention does not require that all the advantageous features or that all the advantages need to be incorporated into every embodiment of the invention. The present embodiments are therefore to be considered in all respects as illustrative and not to be restrictive.

I claim:

1. A method of diagnosing a probability of pain relief through medical treatment in a patient, the method comprising the following steps:
   (a) administering a perceptual test to the patient, the perceptual test including a plurality of declarative statements relating to somatization;
   (b) receiving responses from the patient to the plurality of declarative statements, said responses including an affirmative response and a negative response;
   (c) recording the responses to said plurality of declarative statements on a response sheet;
   (d) providing three scoring templates of pre-selected responses to the plurality of declarative statements, the three scoring templates of pre-selected responses being selected from a group of validity factors comprising defensiveness, predictiveness and carelessness;
   (e) providing six scoring templates of pre-selected responses to the plurality of declarative statements, the six scoring templates of pre-selected responses being selected from a group of clinical factors comprising somatic concern, depressed mode, passive personality, compulsive/obsessive personality, hypomania, and ego integrative defect;
   (f) applying each of said scoring templates from the group of validity factors and the group of clinical factors to the responses to the plurality of declarative statements from the patient, producing a raw score value for each of the validity factors and each of the clinical factors;

(g) recording the raw score value for each of the validity factors and each of the clinical factors on the response sheet;

(h) assessing errors in the test utilizing a carelessness factor raw score;

(i) adjusting each raw score from the group of clinical factors comprising somatic concern, compulsive/obsessive personality, and hypomania, by a percentage of a defensiveness factor raw score, producing adjustment scores for each raw score from said group of clinical factors;

(j) recording the adjustment scores for each raw score from said group of clinical factors on the response sheet;

(k) creating a set of final scores relating to the somatic concern clinical factor, the compulsive/obsessive personality clinical factor, and the hypomania clinical factor;

(l) recording said set of final scores on the response sheet:

(m) preserving a set of raw scores from a group of clinical factors comprising depressed mode, passive personality, and ego integrative defect;

(n) standardizing a score for each of the somatic concern clinical factor final score, the depressed mode clinical factor raw score, the passive personality clinical factor raw score, the compulsive/obsessive personality clinical factor final score, and the hypomania clinical factor final score, utilizing a standardizing analysis of a clinically assessed normative group;

(o) applying a set of scoring rules to a group of clinical factor standardized scores comprising somatic concern, depressed mode, and passive personality;

(p) determining a scoring value of standard deviations above a normative group mean for each said standardized score clinical factor;

(q) applying the set of scoring rules to the ego integrative defect clinical factor raw score, determining a scoring value of standard deviations above the normative group mean for the ego integrative defect clinical factor;

(r) applying the set of scoring rules to a numerical relationship between the scoring value for the somatic concern clinical factor and the scoring value for the compulsive/obsessive personality clinical factor;

(s) determining a scoring value of standard deviations above the normative group mean for said numerical relationship;

(t) applying the set of scoring rules to a numerical relationship between the scoring value for the somatic concern clinical factor and the scoring value for the passive personality clinical factor;

(u) determining a scoring value of standard deviations above the normative group mean for said numerical relationship;

(v) applying the set of scoring rules to a numerical relationship between the scoring value for the depressed mode clinical factor and the scoring value for the hypomania clinical factor;

(w) determining a scoring value of standard deviations above the normative group mean for said numerical relationship;

(x) recording the scoring value for the somatic concern clinical factor, the scoring value for the depressed mode clinical factor, the scoring value for the passive personality clinical factor, the scoring value for the ego integrative defect clinical factor the scoring value for the numerical relationship between the somatic concern clinical factor and the compulsive/obsessive personality clinical factor, the scoring value for the numerical relationship between the somatic concern clinical factor and the passive personality clinical factor, and the scoring value for the numerical relationship between of the depressed mode clinical factor and the hypomania clinical factor on the response sheet;

(y) summing the scoring value for the somatic concern clinical factor, the scoring value for the depressed mode clinical factor, the scoring value for the passive personality clinical factor, the scoring value for the ego integrative defect clinical factor, the scoring value for the numerical relationship between the somatic concern clinical factor and the compulsive/obsessive personality clinical factor, the scoring value for the numerical relationship between the somatic concern clinical factor and the passive personality clinical factor, and the scoring value for the numerical relationship between of the depressed mode clinical factor and the hypomania clinical factor; and (z) thereby producing a single pain index score indicating and measuring the effect of somatization on the patient.

2. A method as in claim 1 and further including the steps of:

(a) establishing a probability equation score for the probability of pain relief through medical treatment by comparing the predictiveness factor raw score to a regression analysis of predictiveness validity factor raw scores to predict percentages of probability of success to medical treatment;

(b) plotting the probability equation score and the pain index score to a graph of divergent linear curves of clinically observed percentage probability values and numerical indices scores for multiple patients;

(c) comparing a relationship between the probability equation score and the pain index score, confirming accuracy and internal validity of the method diagnosing a probability of pain relief through medical treatment in the patient; and (d) thereby producing an outcome analysis graph diagnosing the probability of pain relief through medical treatment in the patient.

* * * * *